(12) United States Patent
White et al.

(10) Patent No.: US 12,678,058 B2
(45) Date of Patent: Jul. 14, 2026

(54) SYSTEM AND METHOD FOR MONITORING A PERSON FOR SIGNS OF SICKNESS

(71) Applicant: Innovative Health Monitoring LLC, Stamford, CT (US)

(72) Inventors: Eric G. White, Tinton Falls, NJ (US); David Robert Abrams, Jersey City, NJ (US); David Eason Smith, Collegeville, PA (US); Jessica Aletta, Manasquan, NJ (US)

(73) Assignee: Innovative Health Monitoring LLC, West Palm Beach, FL (US)

( * ) Notice: Subject to any disclaimer, the term of this patent is extended or adjusted under 35 U.S.C. 154(b) by 0 days.

(21) Appl. No.: 18/519,417

(22) Filed: Nov. 27, 2023

(65) Prior Publication Data

US 2024/0206745 A1 Jun. 27, 2024

Related U.S. Application Data

(63) Continuation of application No. 17/003,773, filed on Aug. 26, 2020, now abandoned, which is a continuation-in-part of application No. 16/239,501, filed on Jan. 3, 2019, now abandoned.

(60) Provisional application No. 62/891,912, filed on Aug. 26, 2019.

(51) Int. Cl.
*A61B 5/0205* (2006.01)
*A61B 5/00* (2006.01)

(52) U.S. Cl.
CPC .......... *A61B 5/0205* (2013.01); *A61B 5/0077* (2013.01); *A61B 5/4809* (2013.01); *A61B 5/743* (2013.01); *A61B 5/746* (2013.01)

(58) Field of Classification Search
CPC ..... A61B 5/746; A61B 5/4809; A61B 5/4812; A61B 5/4815; A61B 5/4818
See application file for complete search history.

(56) References Cited

U.S. PATENT DOCUMENTS

| | | | |
|---|---|---|---|
| 7,403,638 | B2 | 7/2008 | Jeung et al. |
| 7,417,727 | B2 | 8/2008 | Polonskiy et al. |
| 7,502,643 | B2 | 3/2009 | Farringdon et al. |
| | | (Continued) | |

FOREIGN PATENT DOCUMENTS

| | | |
|---|---|---|
| CN | 102835958 A | 12/2012 |
| CN | 103110422 B | 5/2013 |
| | (Continued) | |

*Primary Examiner* — Jayanti K Patel
*Assistant Examiner* — Christopher Kingsbury Glover
(74) *Attorney, Agent, or Firm* — Greenberg Traurig, LLP

(57) ABSTRACT

A system and method of monitoring a person to detect the onset of an illness. A monitoring unit collects biometric data and exchanges that data with a remote electronic device. Using the monitoring device, a person is monitored across multiple days. The biometric data collected determines a statistical profile for the collected data. After the statistical profile is calculated, the person can be actively monitored as he/she sleeps. The monitoring occurs during a sample period of sleep. The biometric data collected during the sample period is averaged to obtain a statistical value. The statistical value is compared to the statistical profile of the biometric data. If the sampled biometric data falls outside the statistical profile, a warning is produced on the electronic device.

20 Claims, 5 Drawing Sheets

(56)              References Cited

U.S. PATENT DOCUMENTS

| | | | |
|---|---|---|---|
| 9,311,715 | B2 | 4/2016 | Rafii et al. |
| 10,327,073 | B1 | 6/2019 | McElhone et al. |
| 2003/0201894 | A1 | 10/2003 | Li |
| 2008/0294019 | A1* | 11/2008 | Tran ....................... G16H 15/00 |
| | | | 600/301 |
| 2012/0022348 | A1* | 1/2012 | Droitcour ........... A61B 5/0816 |
| | | | 600/407 |
| 2014/0142729 | A1 | 5/2014 | Lobb et al. |
| 2014/0297217 | A1 | 10/2014 | Yuen |
| 2015/0141762 | A1* | 5/2015 | Heinrich .............. A61B 5/1128 |
| | | | 600/301 |
| 2016/0094812 | A1 | 3/2016 | Chen |
| 2016/0135734 | A1 | 5/2016 | Schindhelm |
| 2016/0313442 | A1 | 10/2016 | Ho et al. |
| 2016/0367202 | A1 | 12/2016 | Carter et al. |
| 2017/0055877 | A1 | 3/2017 | Niemeyer |
| 2018/0035082 | A1 | 2/2018 | Patil |
| 2019/0159674 | A1* | 5/2019 | Kogure .................. G16H 40/67 |
| 2020/0105400 | A1 | 4/2020 | Alvelda et al. |
| 2020/0359913 | A1* | 11/2020 | Ghodrati .............. A61B 5/1117 |

FOREIGN PATENT DOCUMENTS

| | | |
|---|---|---|
| CN | 104133199 A | 11/2014 |
| JP | 2004537335 A | 12/2004 |
| WO | 2002062282 A1 | 8/2002 |

* cited by examiner

SYSTEM AND METHOD FOR MONITORING A PERSON FOR SIGNS OF SICKNESS

RELATED APPLICATIONS

This application is a continuation of U.S. patent application Ser. No. 17/003,773, filed Aug. 26, 2020, which claims benefit and priority to U.S. Provisional Application No. 62/891,912, filed Aug. 26, 2019, and is a continuation-in-part of U.S. patent application Ser. No. 16/239,501, filed Jan. 3, 2019.

BACKGROUND OF THE INVENTION

1. Field of the Invention

In general, the present invention relates to monitoring equipment and methodologies that can monitor the life signs of a person as that person sleeps. More particularly, the present invention relates to monitoring equipment and methodologies that monitor life signs, collect data, and analyze the data to detect secondary medical issues.

2. Prior Art Description

There are many monitoring systems that can be used in a home to monitor the status of a person. Monitoring can be performed in a home for many reasons, such as to detect if a baby is crying or to detect if an elderly person needs assistance. Most monitoring systems tend to be audiovisual systems. That is, the monitoring system contains a camera to view a person and a microphone to detect if that person is crying, speaking or otherwise making noises. One common monitoring system is a baby monitor. These devices are typically placed in a room and are directed toward a crib or bed. The baby monitor transmits images of the crib or bed, along with any detected audio signals, to a remote receiver. A person viewing the display of the receiver can view any movement in the crib or bed and can hear if the occupant of the crib or bed is crying or making any sounds of distress.

The disadvantages of traditional baby monitor systems are obvious. The baby monitor only detects movement and sound. If a child has a fever, and the baby is sleeping in a still manner, then a traditional baby monitor has no ability to detect the fever. In order to detect a medical condition, such as a fever, heart palpitations or other such conditions that are difficult to detect by eye, a biomedical monitoring system must be used. Biomedical monitoring systems utilize sensors designed to actively monitor a targeted biometric. Biomonitoring systems that use wired sensors are not good candidates for home use. The wires of sensors create strangulation hazards and tripping hazards, may be removed accidentally throughout the night, and can pose a risk of skin infection or even burns. As such, the potential harm of a biomonitoring system can outweigh the potential good. Recognizing the disadvantages of wired systems, improved wireless biomonitoring devices have been developed for in-home use. Some of these biomonitoring devices use low energy, such as radar, lidar, laser light, cameras, ultrasound, and/or piezoelectric sensor pads to monitor a sleeping person. Such systems are sensitive enough to detect heartbeats and the slow expansion and contraction of the chest as a person inhales and exhales. Such prior art monitoring systems are exemplified by Chinese Patent Disclosure No. CN104133199A and Chinese Patent Disclosure No. CN103110422A.

Biomonitoring systems can detect very slight movements. However, a need exists for a biomonitoring system that can monitor a person by detecting the slight movements of breathing and/or heartbeats and then analyze that data for other purposes, such as determining if a person has some adverse medical condition. This need is met by the present invention as described and claimed below.

SUMMARY OF THE INVENTION

The present invention is a system and method of monitoring a person to detect the onset of an illness. A monitoring unit is provided that monitors and collects biometric data, wherein the biometric data being collected is selected from a group which includes respiration rate and heartrate. The monitoring unit exchanges data with a remote electronic device, such as a smart phone.

Using the monitoring device, a person is monitored over a prolonged period of time that extends across multiple days. The biometric data collected is used to determine a statistical profile for the collected data. This statistical profile can be computed using any number of methods, one such method being the arithmetic mean of the data. This statistical profile can be computed on measured biometric data such as respiration rate (RPM) or heartrate (BPM), as well as derived data such as bedtime, wake time, sleep quality, pattern of sleep cycles, pattern of nightly movement, or other measured or derived data. After the statistical profile for the biometric data is calculated, the person can be actively monitored as he/she sleeps. The monitoring occurs during a sample period of sleep that lasts a predetermined period of time. Statistical analysis is applied to the biometric data collected during the sample period to obtain a statistical value. The statistical value can be computed using a method similar to that used in determining the statistical profile, such as use of the arithmetic mean. The statistical value is compared to the statistical profile of the biometric data. If the statistics computed on the sampled biometric data exceeds the statistical profile by a certain predetermined threshold amount, a warning is produced on the electronic device. The warning informs an observer that the person being monitored has a respiration rate and/or heartrate that is abnormal and may be indicative of an illness.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention biomonitoring system can be used in many institutional settings, such as hospitals and nursing homes, the biomonitoring system is particularly well suited for in-home use. Accordingly, an exemplary embodiment of the biomonitoring system is selected for the purposes of description and illustration that shows the present invention being used in a home to monitor a person in a bed or crib. The illustrated embodiment, however, is merely exemplary and should not be considered a limitation when interpreting the scope of the claims.

Figure 1:
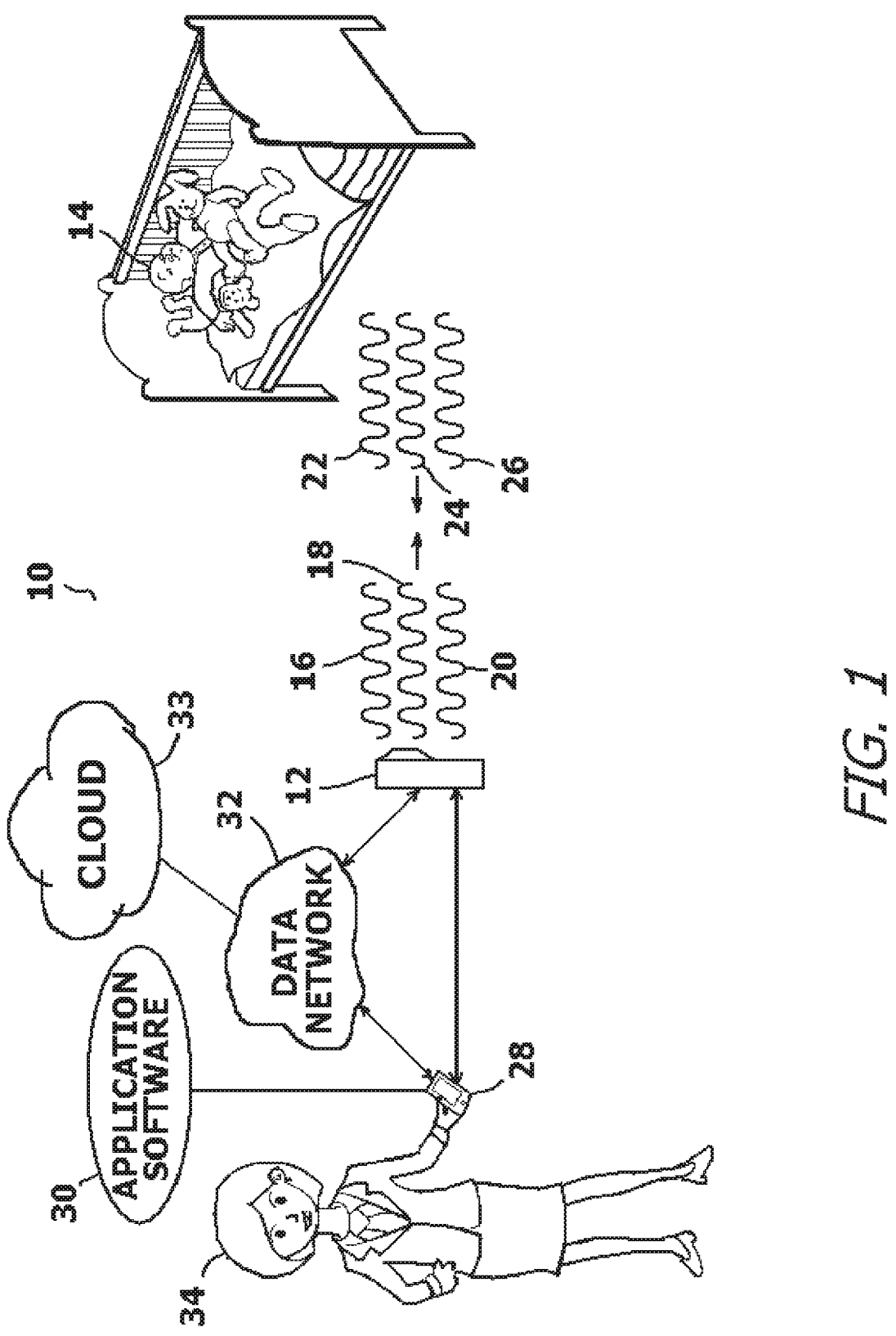
FIG. 1 shows an exemplary embodiment of the present invention biomonitoring system.

Referring to FIG. 1, a biomonitoring system 10 is shown that collects and analyzes data to determine the present or absence of various medical issues in a monitored person 14. The data is collected using a monitoring unit 12. Although a specific monitoring unit 12 is illustrated and described, many prior art monitoring systems can be adapted for use, provided those systems are capable of detecting the respiration rate and/or heartrate of the monitored person 14.

The monitoring unit 12 is placed in a room and is directed toward the monitored person 14, such as a child in a crib or an adult in bed. The monitoring unit 12 used in the exemplary embodiment, can actively emit light 16, radar signals 18 and audio signals 20. The light 16 emitted is preferably in the infrared spectrum so as not to be visible to the monitored person 14. The emitted radar signals 18 are low-energy signals that are harmless to the monitored person 14 and any other sensitive electronic equipment, such as a pacemaker. The emitted audio signals 20 are audible to the monitored person 14 being monitored. As will later be explained, the audio signals 20 can be music, an alarm, or the transmitted voice of another person.

The monitoring unit 12 receives light 22, reflected radar signals 24 and ambient sounds 26. The light 22 received includes existing ambient light and light returned from any illumination projected by the monitoring unit 12. The reflected radar signals 24 are the returns from the radar signals 18 emitted by the monitoring unit 12. The ambient sounds 26 are any audible sounds detected by the monitoring unit 12. The light 22, reflected radar signals 24 and ambient sounds 26 received by the monitoring unit 12 are all internally processed. The monitoring unit 12 uses circuitry and processing software to specifically extract features that are associated with the breathing movements and/or heartbeat movements of the monitored person 14. The monitoring unit 12 processes the light 22, reflected radar signals 24, and ambient sounds 26 in real time. The processed information can be accessed by a remote electronic device 28, such as a smart phone, running the application software 30 needed to display the processed signal information. Depending upon the location of the remote electronic device 28, the processed signals can be shared directly with the remote electronic device 28 or can be forwarded to the remote electronic device 28 through a data network 32, such as a cellular network or the Internet®.

An observer 34, such as a parent or nurse, can view the remote electronic device 28 and receive the processed information. As will later be explained, the processed information is formatted in a user-friendly manner. Likewise, if an alarm condition is detected by the monitoring unit 12, the observer 34 is instantly informed with a warning. The observer 34 can communicate with the monitoring unit 12 and cause the monitoring unit 12 to broadcast music or words that can be heard by the monitored person 14. In such a manner, a monitored person 14 who is agitated can be pacified and a monitored person 14 in distress can be comforted until help arrives on scene.

Figure 2:
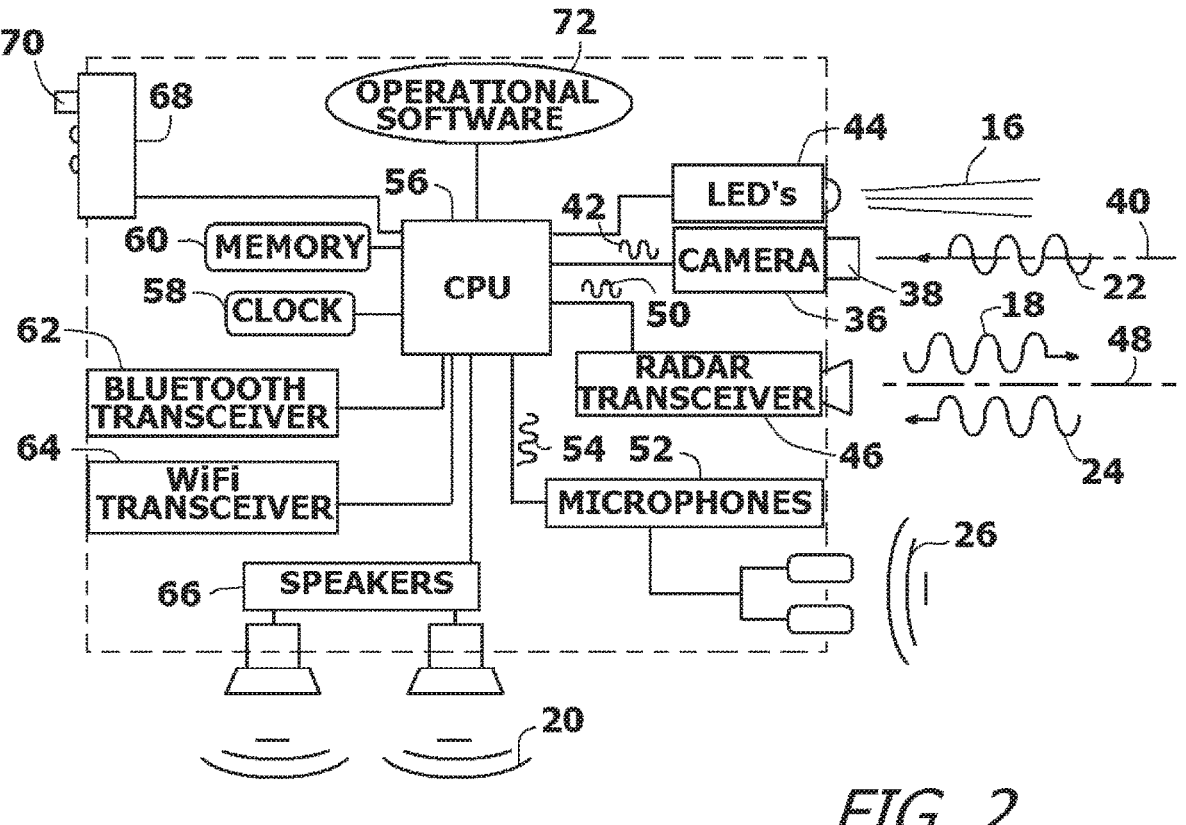
FIG. 2 shows a schematic of the monitoring unit used by the present invention biomonitoring system.

Referring to FIG. 2, the primary components of the monitoring unit 12 are shown and explained. The monitoring unit 12 contains a camera 36 for imaging the sleeping area in a crib, bed, bassinet, or the like. The camera 36 preferably has the ability to image the visible light spectrum and at least some of the infrared spectrum. In this manner, the camera 36 can image in daylight and in the dark.

The camera 36 has an objective lens 38. The objective lens 38 is aimed in a particular direction that is shown by line 40. The objective lens 38 of the camera 36 is directed toward the monitored person 14. The light 22 captured by the camera 36 is converted into camera data 42 that is processed in a manner later described.

One or more LEDs 44 may be provided for illuminating the person 14 being monitored. The LEDs 44 are preferably IR LEDs that produce light that can be detected by the camera 36 but not by the eyes of the person 14 being monitored. It will be understood that the LEDs 44 are an economical source of IR light. However, other sources of IR light, such as low powered IR lasers or filtered polychromatic lights, can also be used in the design. Regardless of the source of the IR light, the intensity of the light is sufficient to illuminate the area of the monitored person 14, therein enabling the camera 36 to image that area.

A radar transceiver 46 is provided. Although different radars can be used, the radar transceiver 46 is preferably a low-powered pulse Doppler radar. In this manner, the radar transceiver 46 can detect both velocity and range. The radar transceiver 46 is configured to have its greatest range in a particular direction 48. The direction 48 of greatest range is parallel to the directional line 40 of the camera 36. As such, the radar transceiver 46 covers the same area being imaged by the camera 36. This causes the radar transceiver 46 to be more sensitive in the direction of the subject area. The radar transceiver 46 emits radar signals 18 covering the subject area and detects reflected radar signals 24 that return. The reflected radar signals 24 are detected by the radar transceiver 46 and are converted into radar data 50. The radar data 50 is processed in a manner that is later described.

One or more microphones 52 are provided as part of the monitoring unit 12. Preferably, at least two microphones 52 are used. The microphones 52 are oriented toward the subject area targeted by the camera 36 and radar transceiver 46. In this manner, any ambient sounds 26 originating within the subject area will be detected by the microphones 52. The microphones 52 produce audio data 54. The audio data 54 is processed in a manner that is later described.

A computing device 56 receives the camera data 42, the radar data 50 and the audio data 54. The computing device 56 contains a clock 58 that enables the data to be indexed by time. The computing device 56 can have a high capacity memory 60 or access to cloud memory 33 through the data network 32 so that large caches of time indexed data can be stored for later review.

The computing device 56 can exchange data with outside sources using a Bluetooth® transceiver 62 and/or a Wi-Fi transceiver 64. Other data transmission systems can also be used, such as cellular network transmissions and/or hardwire connections. The computing device 56 also controls one or more speakers 66. The speakers 66 can broadcast audio signals 20 into the environment of the monitoring unit 12. As will later be explained, the broadcast audio signals 20 can be soothing music that can lull a child to sleep or a piercing alarm that can bring help.

The computing device 56 is also connected to a user interface 68. The user interface 68 contains an on/off switch 70 for the monitoring unit 12 and may contain status lights and sensitivity controls that can be manually adjusted by a user.

The computing device 56 is programmable and runs specialized operational software 72. The operational software 72 is capable of being periodically updated with programming updates received through the Bluetooth® transceiver 62, the Wi-Fi transceiver 64, or another data transmission system.

Figure 3:
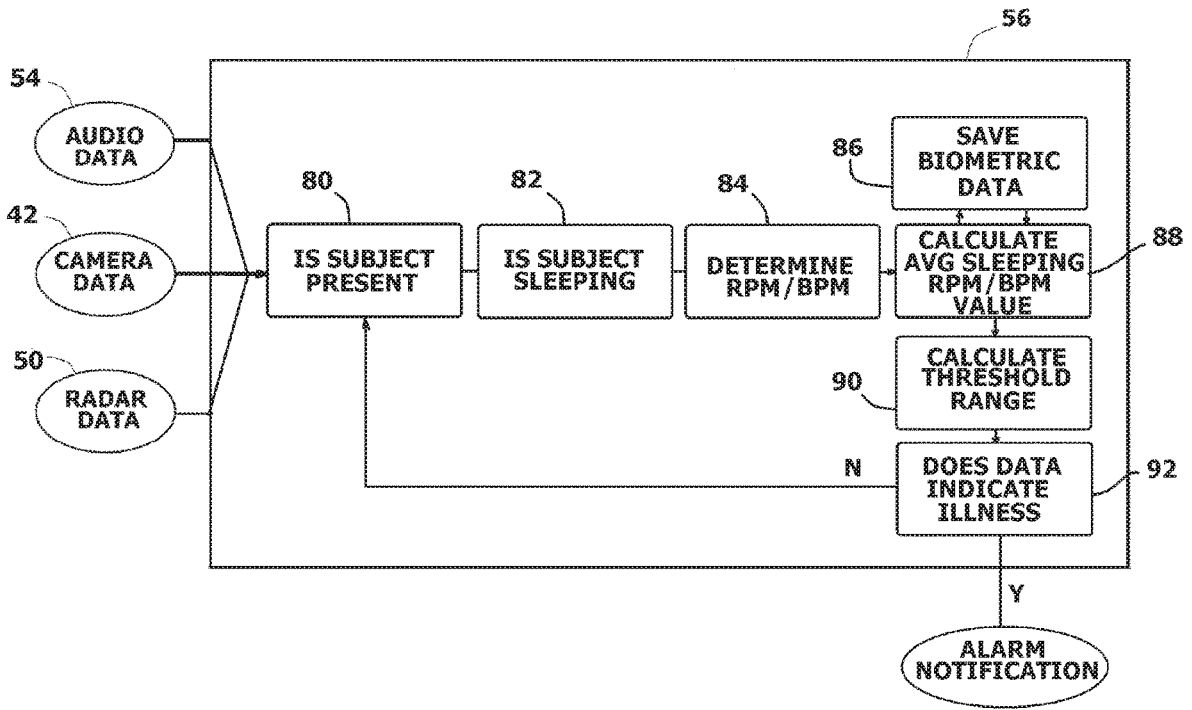
FIG. 3 shows a logic diagram that illustrates the operations performed within the monitoring unit.

Referring to FIG. 3 in conjunction with FIG. 2, it will be understood that the computing device 56 receives the audio data 54 from the microphones 52, the camera data 42 from the camera 36, and the radar data 50 from the radar transceiver 46. This data is analyzed by the computing device 56 using the operational software 72. The purpose of the analysis is to first determine if the person 14 is within the area being monitored. See Block 80. If the subject person 14 is in the monitored area, it will then extract features from within the audio data 54, the camera data 42 and the radar data 50 to determine if they are asleep and to ascertain a reparation rate and/or heartrate for the monitored person 14. See Block 82 and Block 84. The methodology of determining respiration rate and/or heartrate from the audio data 54, the camera data 42 and the radar data 50 is disclosed in co-pending U.S. patent application Ser. No. 16/239,501, filed Jan. 3, 2019, the disclosure of which is herein incorporated by reference.

The isolation of respiration rate and/or heartrate from the audio data 54, the camera data 42 and the radar data 50 enables the operational software 72 to measure the respiration rate in Respirations Per Minute (RPM) and heartrate in Beats Per Minute (BPM). It is a known physiological fact that a person's RPMs and BPMs increase when that person is experiencing a fever. This increase in RPMs and BPMs is detected and used to provide a warning that the monitored person 14 has developed a fever.

A person's respiration rate and heartrate increases and decreases for many reasons, both when a person is awake and when a person is sleeping. For instance, when a person is dreaming, that person experiences rapid eye movement (REM) sleep. During REM sleep, there is an increase in RPMs and BPMs as compared to other non-dream cycles during sleep. In the present invention, the audio data 54, the camera data 42 and the radar data 50 are used to determine if the monitored person 14 is asleep. See Block 82. This can be determined by detecting lack of movement and known sleep rhythm breathing patterns. If the monitored person 14 is asleep, the data regarding that person's natural RPMs and/or BPMs are time stamped and saved. See Block 86. Periods of REM sleep can be saved if such data is desired for analysis. The RPM and/or BPM data is preferably recorded for multiple days and ideally for at least seven days on a rolling basis. However, longer and shorter time periods may be used. The analysis of the data produces a statistical sleeping RPM profile and/or a statistical BPM profile for a particular monitored person 14. See Block 88. Within the data that determines the statistical RPM profile and the statistical BPM profile, there are statistical deviations. The data also contains a calculable margin of error. Both the statistical deviation and the margin of error can be mathematically determined using further statistical analyses. As is indicated by Block 90, a corrected statistical profile is calculated. The threshold range could be, as an example, the sum of the deviation values as corrected by a multiple of the calculated margin of error.

The operational software 72 runs a sickness detection algorithm to determine if the data indicates the presence of some sickness, such as a fever, that effects the normal respiration rate or heartrate of the monitored person 14. See Block 92. The sickness algorithm is run for a sample period of time only when the monitored person 14 is deemed asleep. The preferred threshold range is calculated from multiple nights of data, when the monitored person 14 is known to be healthy. This will provide an accurate range for respiration rate and/or heart rate during healthy sleep.

During sleep, the monitoring unit 12 determines the respiration rate and/or heartrate of the monitored person 14 for a sample period of time (TimeY). Once the monitored person 14 is determined to be fully asleep, the monitored person 14 is scanned for a minimum sample period (TimeX), which is preferably at least fifteen minutes, before a sickness algorithm is applied to the incoming data. An exemplary sickness algorithm for detecting a fever based upon respiration rate is stated below:

$$\text{If ( (TimeX RPM Value)} - \text{(TimeY RPM Value) ) >}$$
$$\text{Threshold Profile)}$$
$$\text{then signal possible sickness.}$$

An alternate algorithm for detecting a fever based upon heartrate would be as follows.

$$\text{If ( (TimeX BPM Value)} - \text{(TimeY BPM Value) ) >}$$
$$\text{Threshold Profile)}$$
$$\text{then signal possible sickness.}$$

In the above examples, a statistical value for the RPM and/or BPM in the sample period is compared to the corrected statistical profile on a running basis. If the monitored person 14 does has a fever, or similar sickness, it is highly likely that the statistical value for the RPM and/or BPM during the monitored sample period would be greater than the corrected statistical profile. This is due to the typical effects caused by fever including increase in both respiration rate and heart rate.

There are certain ailments that can cause a decrease in respiration rate and/or a decrease in heartrate. Similar algorithms can be used to determine if a person's RPM and/or BPM statistical values decreases due to sickness, wherein the measured respiration rate and/or heartrate are analyzed to see if they are less than the limits defined by the statistical profile.

After the execution of a sickness algorithm, it may be determined that the statistical value for the respiration rate and/or the heartrate of the monitored person 14 falls outside the limits defined by the statistical profile. This indicates the presence of a possible illness and a warning signal is produced.

Figures 4, 5:
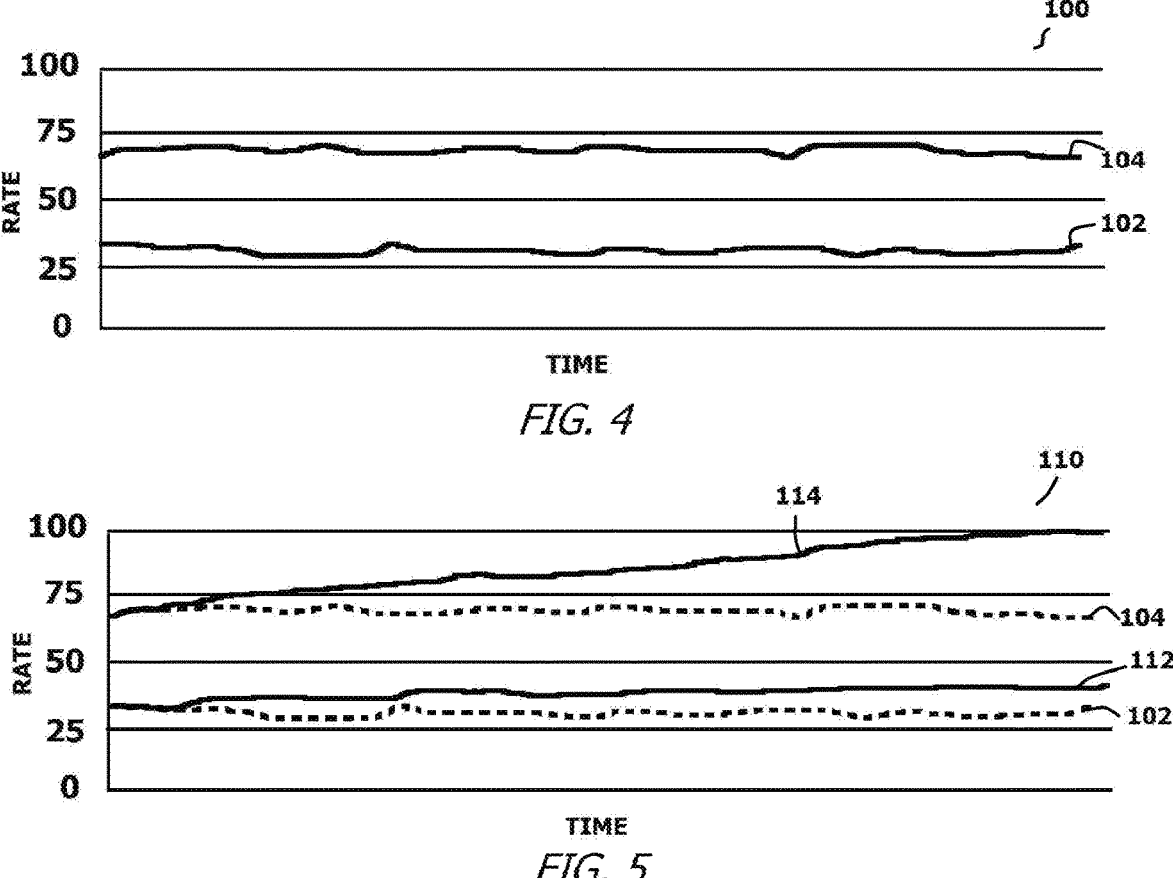
FIG. 4 is an exemplary graph that shows a respiration rate profile and a heartrate profile for a monitored person calculated over multiple overlapping time periods.
FIG. 5 is an exemplary graph that shows data from a person with a fever superimposed over the respiration rate profile and heartrate profile previously plotted in FIG. 4.

Referring to FIG. 4, a graph 100 is shown that plots both respiration rate profile 102 and heartrate profile 104 against time for a person being monitored. The graph 100 of FIG. 4 shows a running average over a period of multiple days.

Referring to FIG. 5, a graph 110 is shown where a current night's data for respiration rate 112 and heartrate 114 are superimposed over the respiration rate profile 102 and heartrate profile 104 previously shown in FIG. 4. The current night's data corresponds to a night when the person being monitored develops a fever. As can be seen both the respiration rate 112 and the heartrate 114 increase to a level well above the statistical profiles. If such a condition lasts for a period of time, a warning signal is generated.

Figure 6:
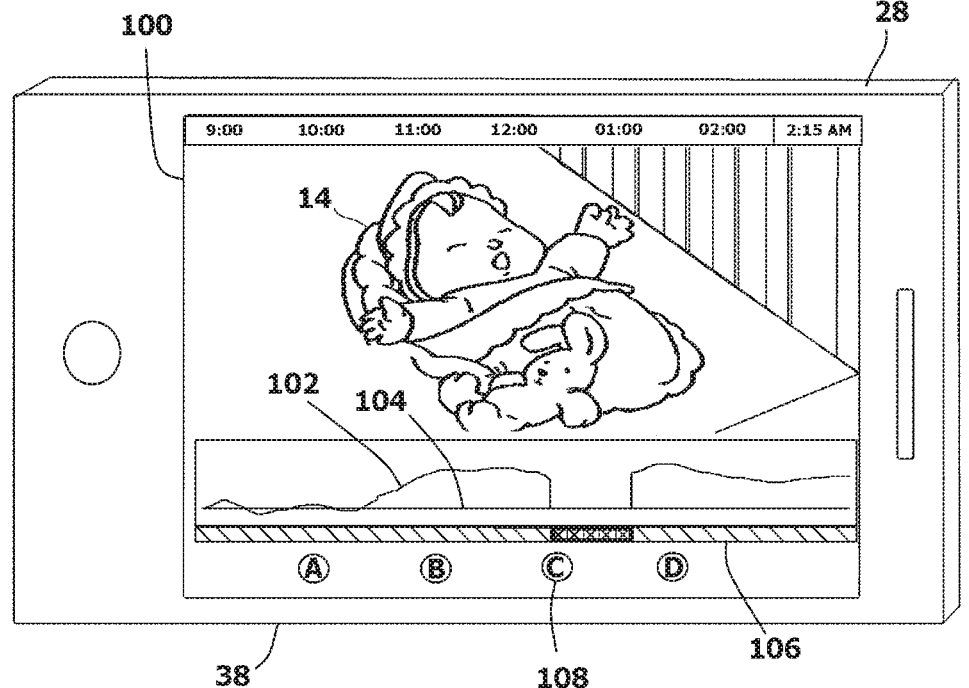
FIG. 6 shows an exemplary screen produced by an electronic device that is used to interface with the monitoring unit of FIG. 2 and a user.

The application software 30 communicates with the remote electronic device 28 via the data network 32. Referring to FIG. 6 in conjunction with FIG. 1, FIG. 2 and FIG. 3, an exemplary screen 100 is shown that exemplifies what a user can see on his/her remote electronic device 28. The screen 100 shows a live feed of the camera data 42. Also, there are various graphs and information bars on the screen 100. A graph 102 is shown that indicates the current RPMs in addition to the recent history of RPMs. A line 104 can also be provided that shows the statistical value for RPMs. It will be understood that similar graphs can be produced for BPMs. Furthermore, the image is time stamped showing the time and date. The user can select different times and dates for comparison. Also, an activity bar 106 is presented. The activity bar 106 shows periods of breathing, movement, non-movement and periods of no data.

Various icons 108 are presented. By pressing the various icons 108, the observer 34 can elect to hear the audio feed from the monitoring unit 12, or send an audio feed to the monitoring unit 12. Furthermore, menu tools are provided so that a user can enter relevant data, such as when the monitored person 14 was administered medications. This information could then be used to determine how long the medication remained effective.

It will be understood that the exemplary algorithms needed to detect sickness only require monitoring respirations per minute and/or heartrate for a statistically significant period of time. This can be accomplished using the monitoring system described. It can also be determined using various commercially available monitoring systems. The methodology of the present invention can therefore be applied to data retrieved using prior art equipment, wherein the methodology employed remains novel. Accordingly, it will be understood that the present invention that is illustrated and described is merely exemplary and that a person skilled in the art can make many variations to that embodiment. All such embodiments are intended to be included within the scope of the present invention as defined by the claims.

What is claimed is:

1. A method of monitoring a living person to detect illness, comprising:

acquiring, via a monitoring unit, sensor data, wherein the sensor data comprises:

radar data from a radar device of the monitoring unit, image data from an image device of the monitoring unit, and audio data from an audio device of the monitoring unit;

detecting, based at least in part on the sensor data, first biometric data representative of the living person;

determining, based at least in part on the first biometric data, a plurality of sleep periods, during which the living person is asleep, throughout a first time period;

determining, based at least in part on the first biometric data, for each sleep period, at least one non-REM sleep stage;

determining, based at least in part on the first biometric data, for each sleep period, at least one non-REM sleep stage-when the living person is sleeping and outside of REM sleep;

generating, from the first biometric data collected during the at least one non-REM sleep stage of each sleep period throughout the first time period, at least one first biometric statistical metric, wherein the at least one first biometric statistical metric comprises a mean value of the first biometric data collected during the at least one non-REM sleep stage of each sleep period throughout the first time period;

generating, from the first biometric data collected during the at least one non-REM sleep stage of each sleep period throughout the first time period, at least one first biometric statistical deviation;

wherein the at least one first biometric statistical deviation of the first biometric data collected during the at least one non-REM sleep stage of each sleep period throughout the first time period;

producing a biometric statistical profile based at least in part on the at least one first biometric statistical metric, the at least one first biometric statistical deviation, and at least one margin of error;

detecting, based at least in part on the sensor data, second biometric data representative of the living person;

determining, based at least in part on the second biometric data, at least one subsequent sleep period during which the living person is asleep;

determining, based at least in part on the second biometric data, for the subsequent sleep period, at least one non-REM sleep stage;

subsequently determining when the living person is sleeping and outside of REM sleep, based on second sensor data; comprising wherein the subsequent sleep period is subsequent to the first time period;

determining, for the at least one non-REM sleep stage during the subsequent sleep period, an illness in the living person based at least in part on a comparison of:

the first biometric statistical profile, and the second biometric data of the subsequent sleep period during the at least one non-REM sleep stage; and outputting a warning indicative of the illness in the living person in response to a deviation of the second biometric data from the first biometric statistical profile.

2. The method of claim 1, wherein the first biometric data includes a first respiration rate.

3. The method of claim 1, wherein the first biometric data includes a first heart rate.

4. The method of claim 1, wherein the outputting includes outputting to a remote electronic device the warning that deviation exceeds a threshold relative to the biometric statistical profile.

5. The method of claim 1, wherein the first image data includes at least one of visible light data or infrared light data.

6. The method of claim 1, wherein the monitoring unit includes a light source, wherein the first image data is based on a reflection of light output by the light source.

7. A method of monitoring a living person to detect illness, comprising:

providing a monitoring unit, wherein the monitoring unit includes a radar device to receive radar data, an image device to receive image data, and an audio device to receive audio data;

determining a first time period during which the living person is sleeping and outside of REM sleep, based on first sensor data comprising:

first radar data from the radar device, first image data from the image device, and first audio data from the audio device, generating, from the first sensor data collected during the first time period, a first biometric statistical distribution based at least in part on first biometric data derived from the first sensor data of the living person, determining a second time period during which the person is sleeping and outside of REM sleep, based on second sensor data comprising second radar data from the radar device,
second image data from the image device, and
second audio data from the audio device,
    wherein the second time period is subsequent to the
      first time period;
generating, for the second time period, second biometric
  data derived from the second sensor data of the living
  person,
  wherein the second biometric data includes at least one
    of a second respiration rate or a second heart rate;
determining, for the second time period, an illness in the
  living person based at least in part on a comparison of:
  a first biometric statistical distribution of the first time
    period during which the living person is sleeping and
    outside of REM sleep, the first biometric statistical
    distribution comprising at least one first mean value
    and at least one first statistical deviation multiplied
    by at least one first error factor, and
  at least one second mean value of the second time
    period during which the living person is sleeping and
    outside of REM sleep;
  determining, based on the comparison, that a deviation
    exceeds a threshold, the deviation being between the at
    least one second mean value and the first biometric
    statistical distribution; and
  outputting warning data, indicative of the person being ill,
    in response to the determining that the deviation
    exceeds the threshold.

8. The method of claim 7, further comprising receiving, with an electronic device, the warning data, wherein the electronic device is separate from the monitoring unit.

9. The method of claim 7, wherein the first biometric data includes the first respiration rate, wherein the second biometric data includes the second respiration rate.

10. The method of claim 7, wherein the first biometric data includes the first heart rate, wherein the second biometric data includes the second heart rate.

11. The method of claim 7, wherein the first image data includes at least one of visible light data or infrared light data.

12. The method of claim 7, wherein the monitoring unit includes a light source, wherein the light source outputs at least one of visible light or infrared light, wherein the first image data is based on a reflection of at least one of the visible light or the infrared light.

13. The method of claim 7, wherein the monitoring unit includes a light source, wherein the light source outputs visible light and infrared light, wherein the first image data is based on a first reflection of the visible light and a second reflection of the infrared light.

14. A method of monitoring a living person to detect illness, comprising:
  providing a remote monitoring unit, wherein the remote
    monitoring unit comprises:
    a radar device to output a radar wave and receive radar
      data corresponding to a reflection of the output radar
      wave,
    an image device to output light and receive image data
      corresponding to a reflection of the output light, and
    an audio device to receive audio data;
  determining at least one first time period during which the
    living person is sleeping and outside of REM sleep,
    based on first sensor data comprising a combination of:
    first radar data corresponding to a reflection of a first
      radar wave output by the monitoring unit,
    first image data corresponding to a reflection of first
      light output by the monitoring unit, and first audio data from the audio device,
  generating, from the first sensor data collected during the
    at least one first time period, a first heart rate statistical
    distribution based at least in part on first heart rate data
    derived from the first sensor data of the living person,
    the first heart rate statistical distributions comprising a
    first heart rate mean value and a first heart rate devia-
    tion associated with the at least one first time period;
  generating, from the first sensor data collected during the
    at least one first time period, a first respiration rate
    statistical distribution based at least in part on first
    respiration rate data derived from the first sensor data
    of the living person, the first respiration rate statistical
    distributions comprising a first respiration rate mean
    value and a first respiration rate deviation associated
    with the at least one first time period;
  generating a first biometric statistical profile associated
    with normal sleeping biometrics of the living person,
    the first biometric statistical profile being based at least
    in part on the first heart rate statistical distribution and
    the first respiration rate statistical distribution;
  determining a second time period during which the person
    is sleeping and outside of REM sleep, based on second
    sensor data comprising:
    second radar data from the radar device,
    second image data from the image device, and
    second audio data from the audio device,
      wherein the second time period is subsequent to the
        first time period;
  generating, from the second sensor data collected during
    the second time period, second biometric data derived
    from the second sensor data of the living person, the
    second biometric data comprising at least one second
    heart rate value and at least one second respiration rate
    value;
  determining, for the second time period, an illness in the
    living person based at least in part on a comparison of:
    the first biometric statistical profile of the first time
      period during which the living person is sleeping and
      outside of REM sleep, and
    the second biometric data of the second time period
      during which the living person is sleeping and out-
      side of REM sleep; and
  determining, based on the comparison, that a deviation
    exceeds a threshold, the deviation being between the
    second biometric data and the first biometric profile;
    and
  outputting an alarm indicative of the person being ill in
    response to the determining that the deviation exceeds
    the threshold.

15. The method of claim 14, further comprising receiving, with an electronic device, warning data associated with the alarm, wherein the electronic device is separate from the monitoring unit; and outputting, by the electronic device, a warning signal, indicative of receipt of the warning data.

16. The method of claim 14, wherein the first biometric data includes a first respiration rate, wherein the second biometric data includes the second respiration rate.

17. The method of claim 14, wherein the first biometric data includes a first heart rate, wherein the second biometric data includes the second heart rate.

18. The method of claim 14, wherein the first image data includes at least one of visible light data or infrared light data.

19. The method of claim 14, wherein the monitoring unit includes a light source, wherein the light source outputs at least one of visible light and infrared light, wherein the first image data is based on a reflection of at least one of the visible light or the infrared light.

20. The method of claim 14, wherein the monitoring unit includes a light source, wherein the light source outputs visible light and infrared light, wherein the first image data is based on a first reflection of the visible light and a second reflection of the infrared light.

\* \* \* \* \*